United States Patent
Gebhard

[11] Patent Number: 6,011,025
[45] Date of Patent: *Jan. 4, 2000

[54] 11-(SUBSTITUTED PHENYL)-ESTRA-4,9-DIENE DERIVATIVES

[75] Inventor: Ronald Gebhard, Oss, Netherlands

[73] Assignee: Akzo Nobel, N.V., Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/935,360

[22] Filed: Sep. 22, 1997

Related U.S. Application Data

[63] Continuation of application No. 08/696,081, Aug. 13, 1996, abandoned.

[30] Foreign Application Priority Data

Aug. 17, 1995 [EP] European Pat. Off. .............. 95202229

[51] Int. Cl.[7] .............................. A61K 31/56; C07J 17/00
[52] U.S. Cl. ........................ 514/178; 514/182; 540/100
[58] Field of Search ............................ 540/100; 514/178, 514/182

[56] References Cited

U.S. PATENT DOCUMENTS 4,634,695  1/1987  Torelli et al. .......................... 514/178

FOREIGN PATENT DOCUMENTS

| 0057115 | 8/1982 | European Pat. Off. . |
|---|---|---|
| 0283428 | 9/1988 | European Pat. Off. . |
| 3717169 | 12/1988 | Germany . |
| WOA 8303099 | 9/1983 | WIPO . |
| WO 95/04536 | 2/1995 | WIPO . |
| WOA 9594536 | 2/1995 | WIPO . |

*Primary Examiner*—Jose' G. Dees
*Assistant Examiner*—Barbara Badio
*Attorney, Agent, or Firm*—Mary E. Gormley

[57] ABSTRACT

The invention relates to a 11-(substituted phenyl)-estra-4,9-diene derivative of formula I

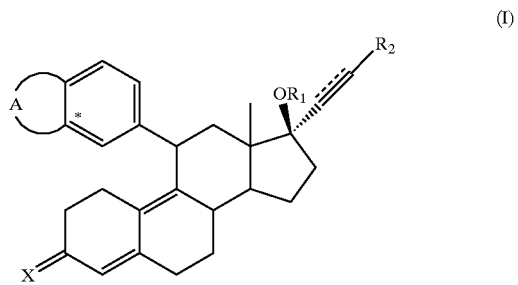

wherein A, X, $R_1$ and $R_2$ are as defined by the specification.

The compounds of the invention have anti-glucocorticoid activity and can be used in treating or preventing glucocorticoid-dependent diseases.

16 Claims, No Drawings

11-(SUBSTITUTED PHENYL)-ESTRA-4,9-DIENE DERIVATIVES

This is a continuation of application Ser. No. 08/696,081 filed Aug. 13, 1996, now abandoned.

The invention relates to a 11-(substituted phenyl)-estra-4,9-diene derivative, a process for the preparation thereof, a pharmaceutical composition containing the same, as well as the use of said derivative for the manufacture of a medicament.

Various 11-(substituted phenyl)-estra-4,9-diene derivatives are known in the art. For example in German Patent DE 3307143 steroids are described which may carry a variety of substituents at the 11-, 13-, 16- and 17-position. According to DE 3307143 these steroid derivatives have marked affinity to the glucocorticoid and progesterone receptor and, in addition, they have reasonable affinity to the androgen receptor. Furthermore, in DE 3307143 it is shown that the steroid derivatives have anti-glucocorticoid activity.

However, Philibert et al. [Agarwal MK (ed): Antihormones in Health and Disease. Front Horm. Res. Basel, Karger, 1991, vol. 19, pp 1–17] discovered that 11-(substituted phenyl)-estra-4,9-diene derivatives disclosed in DE 3307143 are in vivo not very active anti-glucocorticoid steroids (e.g. the 11-(m-methoxyphenyl)- and 11-(m-methylthiophenyl)-derivatives) or have a relatively high progesterone receptor binding affinity (such as the 11-(p-methoxyphenyl)- and 11-(p-methylthiophenyl)-derivatives). These properties seriously restrict the therapeutic potential of the compounds. Low in vivo activity of the derivatives necessitates the administration of high dosages when they are used in therapy. It is very likely that the incidence of adverse side-effects is thereby increased. Furthermore, high progesterone receptor binding affinity may result in (anti) progestagenic activity, which means that the compound may display more than one (anti)hormonal activity, which limits its clinical use, especially for long-term therapy. Thus, there is a need for compounds having high glucocorticoid receptor binding affinity and, in addition, high in vivo anti-glucocorticoid activity, whereas other hormonal activities, such as androgenic and progestagenic activities, are low.

It has now been found that 11-(substituted phenyl)-estra-4,9-diene derivatives of formula I

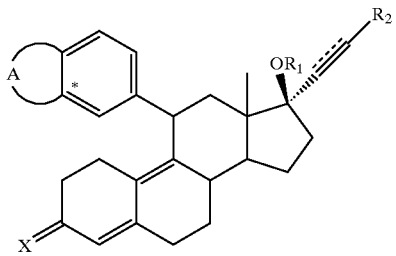

(I)

wherein

A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; $R_1$ is H or 1-oxo(1–4C)alkyl; $R_2$ is H, (1–8C)alkyl, halogen or $CF_3$; X is selected from (H,OH), O, and NOH; and the interrupted line represents an optional bond, show specific and high glucocorticoid receptor binding affinity and are highly active in vivo showing predominant anti-glucocorticoid activity.

The compounds lack appreciable affinity for mineralocorticoid, progesterone, oestrogen and androgen receptors, indicating a clean side effect profile.

The 11-(substituted phenyl)-estra-4,9-diene derivatives of the invention can be used in the prevention and treatment of glucocorticoid dependent diseases or symptoms, like Cushing syndrome, diabetes, glaucoma, sleep disturbances, depression, anxiety, atherosclerosis, hypertension, adiposity, osteoporosis and withdrawal symptoms from narcotics and their mixtures.

Preferred compounds according to this invention are 11-(substituted phenyl) estra-4,9-diene derivatives, wherein the heteroatom(s) are (is) O, the 5- or 6-membered ring being optionally substituted with one or more fluorine atoms; $R_1$ is H; and X is O or NOH.

More preferred compounds are 11-(substituted phenyl) estra-4,9-diene derivatives wherein A is a residue of a 5-membered ring. Particularly preferred are 11-(substituted phenyl) estra-4,9-diene derivatives wherein A contains 2 heteroatoms being O.

Especially preferred are 11-(substituted phenyl) estra-4, 9-diene derivatives wherein $R_2$ is methyl and the interrupted line represents a bond. The most preferred compound is (11β,17β)-11-(1,3-benzodioxol-5-yl)-17-hydroxy-17-(1-propynyl) estra-4,9-dien-3-one.

The term halogen means a fluorine, chlorine, bromine or iodine atom. Fluorine is the preferred halogen in ring A and when $R_2$ is halogen, chlorine is preferred. The terms (1–4C)alkyl and (1–8C)alkyl, as used in the definitions of $R_1$ and $R_2$, respectively, mean alkyl groups having 1–4 and 1–8 carbon atoms, respectively, for example methyl, ethyl, propyl, isopropyl, butyl, sec-butyl, tert-butyl, pentyl, neopentyl, hexyl, octyl.

The 11-(substituted phenyl)-estra-4,9-diene derivatives according to the present invention can be prepared by a process wherein a compound of formula II

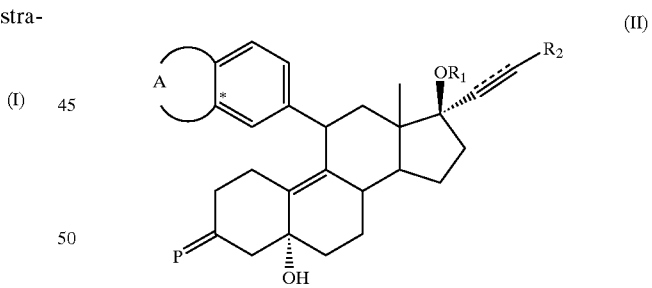

(II)

wherein A, $R_2$ and the interrupted line have the meanings as previously defined, $R_1$ is H, and P is a protected keto-group, is dehydrated and deprotected, after which the 17β-OH is optionally esterified by reaction with an appropriate carboxylic acid to give a derivative wherein $R_1$ is 1-oxo(1–4C)alkyl, and optionally the 3-oxo group is converted into the corresponding 3-hydroxy- or 3-oxime derivative. The 3-oxo group can be reduced to form the 3-hydroxy-derivative by using a suitable reducing agent, such as sodium borohydride. The 3-oxime derivatives can be prepared by hydroxylamine treatment in a suitable solvent, like pyridine.

The derivatives of formula II may be prepared according to well known methods described and used for the preparation of steroids. A suitable process for the preparation of derivatives of formula II starts from estra-4,9-diene-3,17-dione. Selective reduction of the 17-keto group to 17β-OH, 17α-H, e.g. with sodium borohydride, followed by protection of the 3-keto group, e.g. by ketalisation with ethyleneglycol, triethylorthoformate and p-toluenesulfonic acid, and oxidation of the 17-hydroxy group, e.g. with pyridinium chlorochromate, provides the 3-ketoprotected estra-5(10),9(11)-diene-3,17-dione. Alkynylation at the 17-position (yielding a 17α-alkynyl,17β-OH derivative), followed by epoxidation of the 5(10) double bond, e.g. with hydrogen peroxide, trifluoroacetophenone, and pyridine in dichloromethane according to the method as disclosed in European patent application EP 0 298 020, provides the 3-keto-protected St, 5α, 10α-epoxy-17α-alkynyl-17β-hydroxy-estr-9(11)-ene-3-one. Subsequently, compounds of formula II are formed from this epoxide derivative, for example by reaction with an organometallic compound of the formula

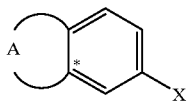

wherein X is a (alkali)metal, like lithium, or a magnesiumhalide, preferably magnesium bromide.

Suitable protective groups and methods to remove these groups are known in the art, for example from T. W. Green: Protective Groups in Organic Synthesis (Wiley, N.Y., 1981). Particularly suitable protective groups for the protection of keto groups are acetals, e.g. 1,2-ethylene ketal.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLE 1

(11β,17β)-11-(1,3-Benzodioxol-5-yl)-17-hydroxy-17-(1-propynyl)estra-4,9-dien-3-one a) A solution of ethyl magnesium bromide (prepared by reacting 19.3 g of Mg (788 mmol) and 58 ml of ethylbromide (775 mmol) in 1 l of THF was cooled to 0–5° C. 83 ml (1.46 mol) of propyn (previously condensed in a dry-ice/acetone-cooled cylinder) was bubbled slowly through this Grignard solution. Subsequently, 50 g (159 mmol) of estra-5(10),9(11)-diene-3,17-dione-3-(cyclic 1,2-ethanediyl acetal) (see EP 0683172), dissolved in 200 ml of THF, was added dropwise to the solution with ice-cooling. Stirring was continued for one hour at ambient temperature. Work-up was accomplished by pouring the mixture into a saturated aqueous ammonium chloride solution, followed by ethyl acetate extraction (2 times). The organic layers were washed with brine, dried with anhydrous magnesium sulfate, filtered and evaporated to give 58.4 g of crude 17α-propynyl-17β-hydroxy-estra-5(10),9(11)-diene-3-one-3-(cyclic-1,2-ethanediyl acetal).

b) The product obtained under a) was dissolved in 809 ml of dichloromethane. Subsequently 4.8 ml of pyridine, 15.2 ml of trifluoroacetophenone and 219 ml of 30% hydrogen peroxide were added and the resulting two-phase system was vigorously stirred at ambient temperature for 36 hours. The mixture was poured into water and the organic layer was separated and washed twice with a saturated sodium thiosulfate solution. Drying with anhydrous magnesium sulfate, filtering and evaporation provided a semi-solid residue. Crystallisation from diethyl ether provided 29.4 g of 5α,10α-epoxy-17α-propynyl-17β-hydroxy-estr-9(11)-ene-3-one-3-(cyclic-1,2-ethanediyl acetal), m.p. 191° C.

c) 534 mg of CuCl were added at 0–5° C. to a solution of 3,4-(methylenedioxo)phenylmagnesium bromide (prepared from 1.9 g (77.6 mmol) of Mg and 9.27 ml (77.0 mmol) of 4-bromo-1,2-(methylenedioxo)benzene in 125 ml dry THF. After stirring for 30 min. at 0–5° C., 9.5 g (25.7 mmol) of 5α,10α-epoxy-17α-propynyl-17β-hydroxy-estr-9(11)-ene-3-one-3-(cyclic-1,2-ethanediyl acetal), dissolved in 125 ml of dry THF were added, while keeping the temperature below 10° C. Stirring was continued for one hour at ambient temperature. Work-up was accomplished by pouring the mixture into a saturated ammonium chloride solution and extraction with ethyl acetate (2 times). The combined organic layers were washed with brine, dried with anhydrous magnesium sulfate, filtered and concentrated. Trituration of the residue with heptane provided 12.25 g of 5α,17β-dihydroxy-11β-[1,3-benzodioxol-5-yl]-17α-propynyl-estr-9-ene-3-one 3-(cyclic 1,2-ethanediyl acetal), pure enough to be used in the next step.

d) 5 g (10.2 mmol) of the compound obtained under 1c) was dissolved in 150 ml of acetone. The solution was cooled to 0–5° C. and after addition of 10 ml of 6N $H_2SO_4$, the mixture was stirred for one hour. Then, the cold solution was poured into a saturated sodium bicarbonate solution and the mixture was extracted with ethyl acetate (2 times). The combined organic layers were washed with brine, dried with anhydrous magnesium sulfate, filtered and concentrated. Chromatography, with heptane/ethylacetate (8/2 v/v %) as eluent, provided 3 g of (11β,17β)-11-(1,3-benzodioxol-5-yl)-17-hydroxy-17-(1-propynyl)estra-4,9-dien-3-one. Crystallisation from diethyl ether afforded 2.4 g of crystals, m.p. 212.6–214° C.

EXAMPLE 2

3E- and 3Z-(11β,17β)-11-(1,3-benzodioxol-5-yl)-17-hydroxy-17-(1-propynyl) estra-4,9-dien-3-one oxime 1.3 g (3 mmol) of the product obtained under example 1d) was dissolved in 33 ml of pyridine. Subsequently, 1.05 g (15 mmol) of hydroxylamine hydrochloride was added and the mixture was stirred at room temperature for 2 hours. The mixture was poured into water, neutralized with dilute hydrochloric acid and extracted with ethyl acetate. The organic layer was washed with brine, dried with magnesium sulfate, filtered and evaporated to dryness. The crude oxime was subjected to chromatographic separation using silicagel and heptane/ethyl acetate 7/3 v/v/ % as eluent. This resulted in 1 g of (3E,11β, 17β)-11-(1,3-benzodioxol-5-yl)-17- hydroxy-17-(1-propynyl)estra-4,9-dien-3-one oxime, having a specific rotation of $[\alpha]^{20}D=+64°$ (c=0.5, dioxane) and 400 mg of (3Z,11β,17β)-11-(1,3-benzodioxol-5-yl)-17-hydroxy-17-(1-propynyl)estra-4,9-dien-3-one oxime, having a specific rotation of $[\alpha]^{20}D=+36°$ (c=0.5, dioxane).

EXAMPLE 3

(11β,17β)-11-(2,3-Dihydro-1,4-benzodioxin-6-yl)-17-hydroxy-17-(1-propynyl)estra-4,9-dien-3-one a) According to the procedure described in example ic), 6.02 g (28 mmol) of 6-bromo-1,4-benzodioxane, 729 mg (30 mmol) of Mg, 90 mg of CuCl and 2.5 g (7 mmol) of the epoxide prepared under example 1b), provided 2.8 g of 5α,17β-dihydroxy-11β-[2,3-dihydro-1,4-benzodioxin-6-yl]-17α-propynyl-estr-9-ene-3-one 3-(cyclic 1,2-ethanediyl acetal).

b) According to the procedure described in example 1d), hydrolysis of the previously obtained material followed by chromatographic purification provided 2.22 g of (11β,17β)-11-(2,3-dihydro-1,4-benzodioxin-6-yl)-17-hydroxy-17-(1-propynyl)estra-4,9-dien-3-one. Crystallisation from diethyl ether/diisopropyl ether gave 1.78 g of crystals, m.p. 200–202° C.

EXAMPLE 4

(11β,17β)-11-(2,2-Difluoro-1,3-benzodioxol-5-yl)-17-hydroxy-17-(1-propynyl) estra-4,9-dien-3-one a) According to the procedure described in example 1c), the Cu-catalyzed Grignard reaction of 5.2 g of 2,2-(difluoromethylene-dioxo)phenylmagnesium bromide [see J. Org. Chem. 37, 673 (1972)] with 2 g of 5α,10α-epoxy-17α-propynyl-17β-hydroxy-estr-9(11)-ene-3-one 3-(cyclic 1,2-ethanediyl acetal) provided 2.7 g of 11β-(2,2-difluoro-1,3-benzodioxol-5-yl)-5α,17β-dihydroxy-17α-propynyl-estr-9-ene-3-one 3-(cyclic 1,2-ethanediyl acetal).

b) According to the procedure described in example 1d), hydrolysis of the previously obtained material followed by chromatographic purification provided 1.5 g of (11β,17α)-11-(2,2-difluoro-1,3-benzodioxol-5-yl)-17-hydroxy-17-(1-propynyl)estra-4,9-dien-3-one, having a specific rotation of $[a]^{20}D=+14°$ (c=1, dioxane).

EXAMPLE 5

(11β,17β)-11-[6-(2,3-Dihydrobenzofuranyl)]-17-hydroxy-17-(1-propynyl)estra-4,9-dien-3-one a) According to the procedure described in example 1c), 4.8 g (24 mmol) of 6-bromo-2,3-dihydrobenzofuran (vide infra), 583 mg (24 mmol) of Mg, 120 mg of CuCl and 2.22 g (6 mmol) of the epoxide prepared under example 1b), provided 2.1 g of 5α,17β-dihydroxy-11β-(2,3-dihydrobenzofuran-6-yl)-17α-propynyl-estr-9ene-3-one 3-(cyclic 1,2-ethanediyl acetal), as a white amorphous material which could be crystallized from diethyl ether.

b) According to the procedure described in example 1d), hydrolysis of the previously obtained material followed by chromatographic purification provided 1.46 g of (11β,17β)-11-[6-(2,3-dihydrobenzofuranyl)]-17-hydroxy-17-(1-propynyl)estra-4,9-dien-3-one as white amorphous material; $[a]^{20}D=+48$ (C=1, dioxane).

6-bromo-2,3-dihydrobenzofuran a) 2,3-dihydro-6-trifluoromethylsulfonyloxy-benzene 4.8 g (10 mmol) of 6-hydroxycoumaran [J. Am. Chem. Soc. 70, 3620 (1948)] and 23.6 g (192 mmol) of N,N-dimethylaminopyridine were dissolved in 400 ml of dry dichloromethane. The solution was cooled to −60° C. and slowly 8.52 ml of triflic anhydride, dissolved in 120 ml of dry dichloromethane, was added dropwise. After stirring at −60° C. for 45 min, the reaction was quenched by pouring it on a saturated sodium hydrogen carbonate solution. Extraction with dichloromethane and drying on sodium sulfate, afforded the crude triflate. Purification using column chomatography (silica gel using heptane/ethyl acetate 9/1 v/v % as eluent) afforded 8.4 g of the pure triflate.

b) 2,3-dihydro-6-trimethylstannyl-benzene 8.04 g (30 mmol) of the previously prepared triflate was dissolved in 135 ml of dioxane; 15 g of hexamethyiditin (45 mmol), 3.81 g (90 mmol) of lithium chloride and 700 mg of $Pd(\phi_3P)_4$ (φ=phenyl) were added and the mixture was refluxed for 17 h. Another portion of 500 mg of $Pd(\phi_3P)_4$ was added and reflux was continued for another 15 h; GC-analysis indicated completion of the reaction. Work-up was accomplished by addition of 45 ml of a 1M potassium fluoride solution in water, stirring for 1 h and filtration over celite. Evaporation and purification by column chromatography afforded 8.1 g of 2,3-dihydro-6-trimethylstannyl-benzene.

c) 6-bromo-2,3-dihydrobenzofuran 8.1 g (28.5 mmol) of 2,3-dihydro-6-trimethylstannyl-benzene was dissolved in 100 ml of dry dichloromethane. The mixture was cooled in ice and slowly a $Br_2$-solution in dichloromethane was added until the orange colour remained (ca. 1 eq. added). The mixture was concentrated and purified using column chromatography using heptane/ethyl acetate 95/5 v/v % as eluent, yielding 4.5 g of 6-bromo-2,3-dihydrobenzofuran as a colourless oil.

EXAMPLE 6

11β,17α-11-(1,3-Benzodioxol-5-yl)-17-hydroxy-19,21,27-trinorcholesta-4,9-dien-20(22)-yn-3-one a) A solution of 3,4-(methylenedioxy)phenylmagnesium bromide, prepared from 11.52 g (473 mmol) magnesium and 57.64 ml (465 mmol) of 4-bromo-1,2-methylenedioxobenzene in 230 ml of THF, was added dropwise to a solution of 46 g (139.5 mmol) of 5α,10α-epoxy-estr-9(11)-ene-3,17-dione 3-(cyclic-1,2-ethanediylacetal) and 2.1 g of CuCl in 465 ml of dry THF at 0–5° C. After stirring for 1 h at 0–5° C., work-up was accomplished by pouring the mixture onto a saturated ammonium chloride solution. Extraction with ethyl acetate and drying with magnesium sulfate afforded the crude 5α-hydroxy-11β-(1,3-benzodioxol-5 -yl)-estr-9(10)-ene-3,17-dione 3-(cyclic-1,2-ethanediylacetal). Purification with column chromatography afforded 56.3 g of the pure product as an amorphous foam.

b) A solution of 7.1 ml of hexyne (60 mmol) in 100 ml of dry THF was treated at −50° C. with 35.8 ml of 1.4 M n-BuLi, followed by dropwise addition of a solution of 4.52 g (10 mmol) of the product obtained under a) in 50 ml of dry THF. The solution was allowed to warm to −20° C. and after 2 h TLC showed the reaction to be complete. Usual work-up afforded 4.9 g of 5α,17β-dihydroxy-11β-(1,3-benzodioxol-5-yl)-17α-hexynyl-estr-9(10)-ene-3,17-dione 3-(cyclic-1,2-ethanediyl-acetal), pure enough to be used in the next step.

Similarly were prepared: b1) 5α,17β-dihydroxy-11β-(1,3-benzodioxol-5-yl)-17α-pentynyl-estr-9(10)-ene-3,17-dione 3-(cyclic-1,2-ethanediylacetal); b2) 5α,17β-dihydroxy-11β-(1,3-benzodioxol-5-yl)-17α-octynyl-estr-9 (10)-ene-3,17-dione 3-(cyclic-1,2-ethanediylacetal) and b3) 5α,17β-dihydroxy-11β-(1,3-benzodioxol-5-yl)-17α-isopentynyl-estr-9(10)-ene-3,17-dione 3-(cyclic-1,2-ethanediylacetal).

c) 1.2 g of the product obtained under b) was dissolved in 60 ml of acetone. The solution was cooled to 0–5° C. and 2.4 ml of a 6N $H_2SO_4$ solution was added. After 1 h, the mixture was neutralized with a 1N NaOH solution, followed by ethyl acetate extraction, drying and evaporation of the solvents.

Purification with chromatography afforded 660 mg of the pure (11β,17α)-11-(1,3-benzodioxol-5-yl)-17-hydroxy-19,21,27-trinorcholesta-4,9-dien-20(22)-yn-3-one; [c]$^{20}$D=26° (C=1, dioxane).

Similarly were prepared: c1) (11β,17β)-11-(1,3-benzodioxol-5-yl)-17-hydroxy-17-(1-pentynyl)estra-4,9-dien-3-one, [a]$^{20}$D=25.8° (C=1, dioxane); c2) (11β,17β)-11-(1,3-benzodioxol-5-yl)-17-hydroxy-17-(1-octynyl)estra-4,9-dien-3-one, [a]$^{20}$D=13.4° (C=0.5, dioxane); c3) (11β,17β)-11-(1,3-benzodioxol-5-yl)-17-hydroxy-19,21-dinorcholesta-4,9-dien-20(22)-yn-3-one, [α]$^{20}$D=22.7° (C=0.5, dioxane).

EXAMPLE 7

(11β,17α,20E)-11-(1,3-Benzodioxol-5-yl)-17-hydroxy-19,21,27-trinorcholesta-4,9,20(22)-trien-3-one a) 342 mg (9 mmol) LiAlH$_4$ was suspended in 35 ml of dry THF; under ice-cooling a solution of 1.6 g of the material obtained in example 6b) was added and the mixture was refluxed for 24 h. Work-up was accomplished by cautious addition of 1.75 ml of a saturated magnesium sulfate solution; stirring was continued for 1 h; then solid magnesium sulfate was added and the mixture was filtered over celite. Evaporation and purification with column chromatography provided 700 mg of the crude 20E-5α,17β,-dihydroxy-11β-[1,3-benzodioxol-5-yl]-17α-(1-hexenyl)-estr-9(10)-ene-3,17-dione 3-(cyclic-1,2-ethanediylacetal).

b) According to the procedure described in example 1d), the previously obtained material was converted into (11β,17α,20E)-11-(1,3-benzodioxol-5-yl)-17-hydroxy-19,21,27-trinorcholesta-4,9,20(22)-trien-3-one, which was obtained as an amorphous solid; [α$^{20}$D]=75.7 (C=1, dioxane).

EXAMPLE 8

(11β,17α,20Z)-11-(1,3-Benzodioxol-5-yl)-17-hydroxy-19,21,27-trinorcholesta-4,9,20(22)-trien-3-one a) 1.9 g of the material obtained in example 6b) was dissolved in 50 ml of ethyl acetate; 171 mg Lindlar catalyst was added and the mixture was shaken in a hydrogen atmosphere untill the absorption stopped. The mixture was filtered over celite and evaporated, giving the almost pure 20Z,5α,17β-dihydroxy-11β-[1,3-benzodioxol-5-yl]-17α-(1-hexenyl)-estr-9(10)-ene-3,17-dione 3-(cyclic-1,2-ethanediylacetal).

b) According to the procedure described in example 1d), the previously obtained material was converted into the desired (11β,17α,20Z)-11-(1,3-benzodioxol-5-yl)-17-hydroxy-19,21,27-trinorcholesta-4,9,20(22)-trien-3-one, which was obtained as an amorphous solid; [α]$^{20}$D=107° (C=0.5, dioxane).

EXAMPLE 9

(11β,17α)-11-(1,3-Benzodioxol-5-yl)-21-chloro-17-hydroxy-19-norpregna-4,9-dien-20-yn-3-one a) 12 ml of a 2.2 M solution of methyllithium in diethylether was cooled to 0° C. To this solution 1.32 g of trans-1,2-dichloroetheen, dissolved in 5.5 ml diethylether, was added slowly, thereby keeping the temperature below 10° C. Stirring was continued for 1.5 h at ambient temperature; during this time a white suspension of LiCl formed. Then, 1.5 g of the steroid obtained in example 6a), dissolved in dry toluene, was added and the mixture was refluxed for 2.5 hrs. TLC indicated completion of the reaction. Work-up was accomplished by pouring the mixture onto a saturated ammonium chloride solution, extraction with ethyl acetate, drying and evaporation, yielding 1.5 g of the crude 5α,17β-dihydroxy-11β-[1,3-benzodioxol-5-yl]-17α-chloroethynyl-estr-9(10)-ene-3,17-dione 3-(cyclic-1,2-ethanediylacetal), as white glass.

b) The material obtained in the previous experiment was converted into the crude (11β,17α)-11-(1,3-benzodioxol-5-yl)-21-chloro-17-hydroxy-19-norpregna-4,9-dien-20-yn-3-one according to the procedure described in example 1d). Crystallization from diethyl ether afforded 464 mg of the pure compound; m.p.: 209° C.

EXAMPLE 10

(11β,17α)-11-(1,3-Benzodioxol-5-yl)-21-trifluoromethyl-17-hydroxy-19-norpregna-4,9-dien-20-yn-3-one a) According to the procedure described in J. Org. Chem. 19, 6051 (1995), 2 g (4.4 mmol) of the steroid prepared in example 6a), 1.94 g (11 mmol) of 1-bromo-1-trifluoromethylethene and 20 mmol LDA (prepared from 12.5 ml n-BuLi, 1.6 M. solution and 3.1 ml N,N-diisopropylamine) were converted into 5α,17β-dihydroxy-11β-[1,3-benzodioxol-5-yl]-17α-trifluoropropynyl-estr-9(10)-ene-3,17-dione 3-(cyclic-1,2-ethanediylacetal); yield after purification with column chromatography (heptane/ethyl acetate 1/1 v/v %): 2 g.

b) The material obtained in the previous step was converted into the crude (11β,17α)-11-(1,3-benzodioxol-5-yl)-21-trifluoromethyl-17-hydroxy-19-norpregna-4,9-dien-20-yn-3-one according to the procedure described in example 1d). After purification with chromatography, 800 mg of the pure compound was obtained as an amorphous material. [α$^{20}$D]=38.1 (C=0.5, dioxane).

EXAMPLE 11

In the following Table the receptor affinity of the compounds of the invention for glucocorticoid receptors (GR) related to progesterone receptors (PR) is presented. The glucocorticoid affinity of the compounds was measured for glucocorticoid receptors present in intact human multiple myeloma cells and compared with the affinity of dexamethasone (according to the procedure described by H. J. Kloosterboer et al., J. Steroid Biochem., Vol. 31, 567–571 (1988)). The progesterone affinity of the compounds was measured for cytoplasmic progesterone receptors present in human breast tumor cells and compared with the affinity of (16α)-16-ethyl-21-hydroxy-19-norpreg-4-ene-3,20-dione (according to the procedure described by E. W. Bergink et al., J. Steroid Biochem., Vol. 19, 1563–1570 (1983)).

| example | GR | PR | GR/PR |
|---------|-----|-----|-------|
| 1 | 189 | 6.4 | 30 |
| 3 | 312 | 5.9 | 53 |

From this Table it can be concluded that the 11-(substituted phenyl) estra-4,9-diene derivatives of the invention show specific and high glucocorticoid receptor affinity.

EXAMPLE 12

The antiglucocorticoid activity of the compounds of the invention has been demonstrated by several tests, e.g. according to the procedure described by H. J. Kloosterboer et al., J. Steroid Biochem., Vol. 31, 567–571 (1988). Body weight, adrenal, thymus and spleen weights were the parameters used. Results of this latter test: at a dose of 20 mg/kg the compound of example 1 inhibited significantly the effect of dexamethasone in all four parameters.

I claim:
1. An 11-(substituted phenyl)-estra-4,9-diene derivative of formula 1

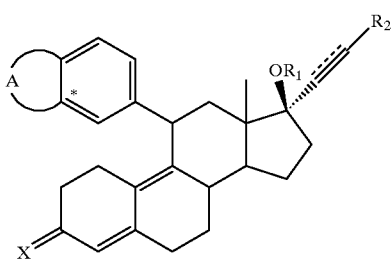

(I)

wherein
A is a 5- or 6-membered saturated ring containing 2 heteroatoms which are not connected to each other and are independently selected from O and S, the ring being optionally substituted with one or more halogen atoms, or A is a saturated 5-membered ring containing 1 heteroatom selected from O and S, which heteroatom is connected to the phenyl group at the position indicated with an asterisk;
$R_1$ is H;
$R_2$ is methyl;
X is selected from O and NOH;
and the interrupted line represents an optional bond.

2. The 11-(substituted phenyl)-estra-4,9-diene derivative of claim 1, wherein the heteroatom(s) are (is) O.

3. The 11-(substituted phenyl)-estra-4,9-diene derivative of claim 1, wherein A is a 5-membered ring.

4. The 11-(substituted phenyl)-estra-4,9-diene derivative of claim 1, wherein A contains 2 heteroatoms and the 2 heteroatoms are O.

5. The 11-(substituted phenyl)-estra-4,9-diene derivative of any one of claims 1–4, wherein the interrupted line represents a bond.

6. The 11-(substituted phenyl)-estra-4,9-diene derivative of claim 1, having the formula (11β,17β)-11-(1,3-benzodioxol-5-yl)-17-hydroxy-17-(1-propynyl) estra-4,9-dien-3-one.

7. The 11-(substituted phenyl)-estra-4,9-diene derivative of claim 2, wherein A is a 5-membered ring.

8. The 11-(substituted phenyl)-estra-4,9-diene derivative of claim 2, wherein A contains 2 heteroatoms, and the 2 heteroatoms are O.

9. The 11-(substituted phenyl)-estra-4,9-diene derivative of claim 3, wherein A contains 2 heteroatoms, and the 2 heteroatoms are O.

10. The 11-(substituted phenyl)-estra-4,9-diene derivative of claim 7, wherein A contains 2 heteroatoms, and the 2 heteroatoms are O.

11. The 11-(substituted phenyl)-estra-4,9-diene derivative of claim 5, (11β,17β)-11-(2,3-dihydro-1,4,benzodioxin-6-yl)-17-hydroxy-17-(1-propynyl)estra-4,9-dien-3-one.

12. A pharmaceutical composition comprising the 11-(substituted phenyl)-estra-4,9-diene derivative of claim 1 and pharmaceutically suitable auxiliaries.

13. The pharmaceutical composition of claim 12, wherein the 11-(substituted phenyl)-estra-4,9-diene derivative is (11β,17β)-11-(2,3-dihydro-1,4,benzodioxin-6-yl)-17-hydroxy-17-(1-propynyl)estra-4,9-dien-3-one.

14. A method for the treatment of glucocorticoid-dependent syndromes, comprising administering an anti-glucocorticoid effective amount of a composition comprising a compound according to claim 1.

15. A method of preparation of the 11-(substituted phenyl)-estra-4,9-diene derivative of claim 1, wherein a compound of formula II

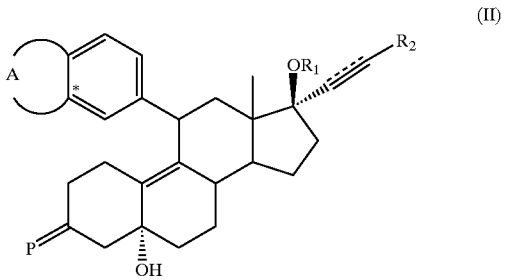

(II)

wherein A, $R_1$, $R_2$ and the interrupted line have the meanings as defined in claim 1, and P is a protected keto-group, is dehydrated and deprotected.

16. The method of claim 15, further comprising converting the 3-oxo group into the corresponding 3-oxime derivative.

* * * * *